United States Patent [19]

Holstedt et al.

[11] Patent Number: 4,490,265

[45] Date of Patent: * Dec. 25, 1984

[54] LUBRICATING COMPOSITIONS

[75] Inventors: Richard A. Holstedt, Whittier, Calif.; Peter Jessup, Millington, N.J.

[73] Assignee: Union Oil Company of California, Los Angeles, Calif.

[*] Notice: The portion of the term of this patent subsequent to Jan. 24, 2001 has been disclaimed.

[21] Appl. No.: 434,602

[22] Filed: Oct. 15, 1982

Related U.S. Application Data

[63] Continuation-in-part of Ser. No. 329,384, Dec. 10, 1981, Pat. No. 4,427,560, and a continuation-in-part of Ser. No. 329,385, Dec. 10, 1981.

[51] Int. Cl.$^3$ .............................................. C10M 1/38
[52] U.S. Cl. .................................. 252/47.5; 252/49.6; 252/49.7; 260/462 R
[58] Field of Search ................... 252/47.5, 48.6, 49.6, 252/32.7 E, 49.7; 568/6; 260/462 R, 462 A, 462 C

[56] References Cited

U.S. PATENT DOCUMENTS

| | | | |
|---|---|---|---|
| 2,441,063 | 5/1948 | Gilmann | 260/401 |
| 3,224,971 | 12/1965 | Knowles et al. | 252/46.3 |
| 3,285,855 | 11/1966 | Dexter et al. | 252/57 |
| 3,692,681 | 9/1972 | Liston | 252/51.5 A |
| 3,929,652 | 12/1975 | Seni et al. | 252/46.7 |
| 3,977,986 | 8/1976 | Conte et al. | 252/47.5 |
| 4,427,560 | 1/1984 | Holstedt et al. | 252/42.7 |

FOREIGN PATENT DOCUMENTS 1520743  8/1978  United Kingdom .............. 252/47.5

*Primary Examiner*—Delbert E. Gantz
*Assistant Examiner*—A. Pal
*Attorney, Agent, or Firm*—Dean Sandford; Gregory F. Wirzbicki; Cleveland R. Williams

[57] ABSTRACT

Lubricating compositions containing an oxidation inhibitor, copper and lead corrosion inhibitors and boron-containing heterocyclic compounds or metal derivatives thereof, which have extreme pressure, anti-wear and friction reducing properties are disclosed.

46 Claims, No Drawings

LUBRICATING COMPOSITIONS

RELATED APPLICATIONS

This application is a continuation-in-part of copending application Ser. No. 329,384 now U.S. Pat. No. 4,427,560 and Ser. No. 329,385, both applications filed on Dec. 10, 1981.

BACKGROUND OF THE INVENTION

1. Field of the Invention

This invention relates to lubricating oils and more particularly to improved lubricating oils containing additives, such as corrosion inhibitors, oxidation inhibitors and extreme pressure, anti-wear and friction reducing compounds.

2. Description of the Prior Art

It is well recognized in the petroleum industry that boron containing compounds are desirable additives for lubricating oils. One such boron containing compound is disclosed in U.S. Pat. No. 3,224,971 to Knowles et al. which relates to intracomplexed borate esters and to lubricating compositions containing said esters. The borate esters are organo-boron compounds derived from boric acid and a bis (o-hydroxy-alkylphenyl) amine or sulfide. These compounds are described as additives for lubricating oils.

Boric-acid-alkylolamine reaction products and lubricating oils containing the same are disclosed in U.S. Pat. No. 3,227,739 to Versteeg. These amine type products are prepared by reacting equal molar proportions of diethanolamine or dipropanolamine and a long chain, 1,2-epoxide. The intermediate reaction product thus produced is reacted with boric acid to produce the final reaction product. These compounds are added to lubricants to prevent rust formation in copper and lead bearings.

As can readily be determined from the above, there is an ongoing effort to develop lubricating compositions having improved properties.

Accordingly, it is an object of the present invention to provide an improved lubricating composition having enhanced extreme pressure, anti-wear and friction reducing properties.

Yet another object of the present invention is to provide a lubricating composition having improved copper and lead corrosion properties.

A further object of the present invention is to provide a lubricating composition containing extreme pressure, anti-wear, friction reducing and corrosion prevention additives, and in addition, an anti-oxidant to prevent attack of oxidants upon metal bearings.

Other objects and advantages of the invention will be apparent from the following description.

SUMMARY OF THE INVENTION

Lubricating compositions of the present invention comprise a major amount of a lubricating oil and a minor amount of:

(A) an extreme pressure, anti-wear and friction reducing boron-containing heterocyclic compound having the formula:

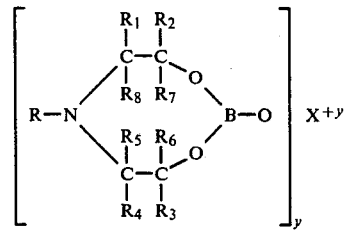

where R is hydrogen or an alkyl, alkene, alkadiene, aryl, alkylaryl or arylalkyl radical having from 1 to 24 carbon atoms, $R_1$, $R_2$, $R_3$ and $R_4$ are the same or different radicals selected from hydrogen or an alkyl, aryl, alkylaryl or arylalkyl radicals having from 1 to about 30 carbon atoms, wherein at least one of said $R_1$, $R_2$, $R_3$ or $R_4$ is an aryl, alkylaryl or arylalkyl radical having from about 6 to about 30 carbon atoms, $R_5$, $R_6$, $R_7$ and $R_8$ are the same or different radicals selected from hydrogen or an alkyl group having from 1 to about 6 carbon atoms, y is an integer between 1 and 4, and x is hydrogen or a metal selected from a transition metal having an atomic number of 21 through 30 or a Group IVA metal;

(B) A copper corrosion inhibitor comprising a compound having the formula:

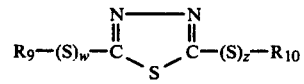

wherein $R_9$ and $R_{10}$ are moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different integers between 1 and 8;

(C) A lead corrosion inhibitor comprising terephthalic acid; and (D) An oxidation inhibitor selected from the group consisting of:

(i) a metal additive having the formula:

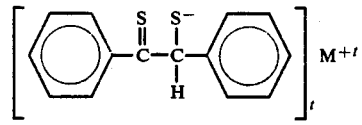

wherein M is a first row transition metal and t is an integer between 1 and 4, and (ii) sulfur bridged, bis hindered phenols having the formula:

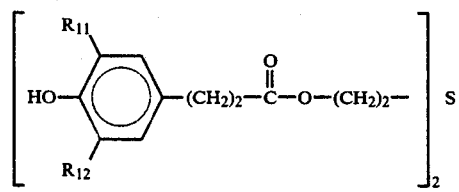

wherein $R_{11}$ and $R_{12}$ are the same or different alkyl groups having from 1 to 6 carbon atoms.

The above-described, boron containing heterocyclic compounds impart extreme pressure, anti-wear, friction reducing, properties to lubricating oils when added to said oils at use concentrations.

DETAILED DESCRIPTION OF THE INVENTION

The present invention resides in lubricating compositions having extreme pressure, anti-wear, friction reducing, corrosion inhibition and anti-oxidant properties which comprise a major amount of a lubricating oil and a minor amount of a mixture comprising a boron-containing heterocyclic compound or a metal derivative of said compound, a hydrocarbon polysulfide derivative of 2,5-dimercapto-1,3,4-thiadiazole, terephthalic acid and a bis(dithiobenzil) metal derivative, or a sulfur bridged, bis hindered phenol or a mixture thereof.

Primary amines useful in preparing the boron-containing heterocyclic compounds (herein denominated boramid compounds) and metal derivatives (metal boramids) of this invention are obtainable commercially or may be produced by reacting alkyl, aryl, alkylaryl or arylalkyl halides with ammonia using conventional techniques and apparatus. These halides react with ammonia at moderately high temperatures and under pressure to produce a mixture of primary, secondary and tertiary amines. The primary amine yield of this process may be improved by using an excess of ammonia in the reaction.

Another typical process for producing primary amines consists of reacting alcohols with ammonia in the vapor phase at temperatures of from 570° F. to 940° F. under 200 to 1,000 p.s.i.g. For the lower molecular weight alcohols, temperatures of 750° F., pressures of about 200 p.s.i.g. and a reaction time of 2 to 3 hours are desirable. The alcohols and ammonia may be conveniently obtained from commercial sources. A mixture of primary, secondary and tertiary amines is formed wherein the amines exist in equilibrium with each other. It is possible to improve the yield of the desired amine by recycling undesired amines through the vapor phase. These primary amines are, in addition, commercially available.

Unsaturated primary amines are conventionally prepared by reacting an unsaturated fatty acid with ammonia to produce an ammonium soap. The ammonium soap is heated to produce an amide. The amide thus produced is heated in the presence of a standard dehydration catalyst to produce a nitrile. The nitrile is contacted with hydrogen gas at increased temperature to produce either an unsaturated amine or a saturated amine depending upon the degree of hydrogenation the nitrile is subjected to.

Primary amines useful in preparing the boramid compounds of the present invention have the chemical formula $RNH_3$ wherein R is an organic radical, preferably where R contains no more than 30 carbon atoms. Among the suitable amines are methyl amine, ethylamine, propylamine, butylamine, octadecyl amine, cyclohexylamine, dodecylamine, phenylamine, oleylamine, cocoamine and tallowamine and mixtures thereof.

In preparing the boramid compounds, these primary amines are reacted with an aromatic oxide to produce an aryloxylated primary amine. Aromatic oxides suitable for use herein preferably have the formula:

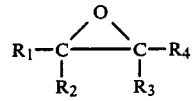

wherein at least one of said $R_1$, $R_2$, $R_3$ or $R_4$ is aryl, alkylaryl or arylalkyl having 6 to 30 carbon atoms with the remaining R groups being independently hydrogen or an organic radical having 1 to 30 carbon atoms, preferably hydrogen or an alkyl radical having 1 to 6 carbon atoms.

Suitable aromatic oxides may be obtained from a commercial source or prepared by three general methods: (1) direct oxidation of aromatic olefins in the presence of a conventional oxidation catalyst; (2) reaction of aromatic olefins with peroxy acids; and (3) hydrolysis of chlorohydrins with bases.

A wide variety of aromatic oxides may be used to prepare the aryl-oxylated primary amines needed to produce the boramid compounds herein. Typical aromatic oxides for use herein include styrene oxide, alpha methyl styrene oxide, para tertiary butyl styrene oxide, cresyl oxide including ortho methyl styrene oxide and para methyl styrene oxide and mixtures thereof.

The primary amine is normally reacted with the aromatic oxide in the presence of a solvent, for example, toluene, methanol or water to produce a diaryloxylated amine. The solvent is added in sufficient quantity to dissolve or disperse the reactants to insure better contact thereof.

Generally the primary amine and aromatic oxide are reacted at a pressure of from about atmospheric pressure to about 500 p.s.i.g. at a temperature of from 176° F. to 450° F., for 1 to 30 hours. The primary amine is preferably reacted with the aromatic oxide at a molar ratio of 1:2 to produce a diaryloxylated amine. It should be noted that aryloxylated amines herein include the aryl, alkylaryl and arylalkyl species of the amine, as well as the diaryloxylated forms. It may be desirable to react the primary amine with two different aromatic oxides to produce a mixed aryloxylated amine. In this embodiment of the invention, one mole of the primary amine is reacted with one mole each of two different aromatic oxides to produce the desired mixed oxide amine. Yet another method of producing the desired aryloxylated amine involves reacting one mole of an aromatic oxide and one mole of an alkene oxide, for example ethylene oxide, with a primary amine to produce a dioxylated amine having an aromatic moiety and an alkyl moiety attached to the nitrogen atoms of the primary amine.

Next, the diaryloxylated amine or mixed diaryloxylated amine is reacted with boric acid at a molar ratio of from about 1:2 to about 1:1 in the presence of a solvent, for example, xylene, benzene, toluene, or the like, to produce a boron containing heterocyclic compound of the present invention, i.e., a boramid compound. Normally, the solvent will comprise from about 20 to about 50 weight percent, preferably from about 30 to about 40 weight percent of the reaction mixture. The reaction is conducted under reflux at a temperature of from 176° F. to 450° F., preferably from 176° F. to 300° F., at a pressure of from atmospheric pressure to about 500 p.s.i.g. for about 1 to about 30 hours. The boramid compound thus produced will contain from about 0.5 to about 10 weight percent, preferably from about 2 to about 5 weight percent of boron. In a preferred mode the primary amine and aromatic oxide are first reacted together and the intermediate reaction product thus produced is, next, reacted with boric acid. An alternate method of producing the boron containing heterocyclic compounds herein involves reacting the primary amine, aromatic oxide and boric acid in a one-step process.

Boron containing heterocyclic compounds prepared in accordance with the procedure herein have the following formula:

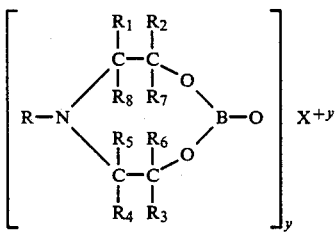

where R is hydrogen or an alkyl, alkene, alkadiene, aryl, alkylaryl or arylalkyl radical having for 1 to 24 carbon atoms, $R_1$, $R_2$, $R_3$ and $R_4$ are the same or different radicals selected from hydrogen or an alkyl, aryl, alkylaryl or arylalkyl radical having from 1 to about 30 carbon atoms, wherein at least one of said $R_1$, $R_2$, $R_3$ or $R_4$ is an aryl, alkylaryl or arylalkyl radical having from about 6 to about 30 carbon atoms, $R_5$, $R_6$, $R_7$ and $R_8$ are the same or different radicals selected from hydrogen or an alkyl group having from about 1 to about 6 carbon atoms, y is an integer between 1 and 4, and x is hydrogen or a metal selected from a transition metal having an atomic number of 21 through 30 or a Group IVA metal.

Preferably, at least one of $R_1$, $R_2$, $R_3$ or $R_4$ is an aryl, alkylaryl or arylalkyl radical having from about 6 to about 20 carbon atoms with the aryl species being especially preferred. Preferably $R_5$, $R_6$, $R_7$ and $R_8$ are hydrogen or an alkyl group having from 1 to about 4 carbon atoms. In an especially preferred mode, at least two of said $R_1$, $R_2$, $R_3$ or $R_4$ are aryl, alkylaryl or arylalkyl radicals having from about 6 to about 20 carbon atoms, and are preferably from 6 to 15 carbon atoms.

Representative heterocyclic, boramid compounds produced in accordance with the procedure herein include the following compounds: 1-hydroxy-3,7-diphenyl-5-dodecyl-5-aza-1-bora-2,8-dioxacyclooctane; 1-hydroxy-4,6-diphenyl-5-dodecyl-5-aza-1-bora-2,8-dioxacyclooctane; 1-hydroxy-4,7-diphenyl-5-dodecyl-5-aza-1-bora-2,8-dioxacyclooctane; 1-hydroxy-3,7-dicresyl-5-dodecyl-5-aza-1-bora-2,8-dioxacylooctane; 1-hydroxy-4,6-dicresyl-5-dodecyl-5-aza-1-bora-2,8-dioxacyclooctane; 1-hydroxy-4,7-dicresyl-5-dodecyl-5-aza-1-bora-2,8-dioxacylooctane; 1-hydroxy-3,7-dimethyl-3,7-diphenyl-5-dodecyl-5-aza-1-bora-2,8-dioxacyclooctane; 1-hydroxy-4,6-dimethyl-4,6-diphenyl-5-dodecyl-5-aza-1-bora-2,8-dioxacyclooctane; 1-hydroxy-4,7-dimethyl-4,7-diphenyl-5-dodecyl-5-aza-1-bora-2,8-dioxacyclooctane; 1-hydroxy-3,7-para tertiarybutylphenyl-5-dodecyl-5-aza-1-bora-2,8-dioxacyclooctane; 1-hydroxy-4,6-para tertiarybutylphenyl-5-dodecyl-5-aza-1-bora-2,8-dioxacyclooctane; 1-hydroxy-4,7-para tertiarybutylphenyl-5-dodecyl-5-aza-1-bora-2,8-dioxacyclooctane; 1-hydroxy-3,7-diphenyl-5-coco-5-aza-1-bora-2,8-dioxacyclooctane; and 1-hydroxy-3,7-diphenyl-5-tallow-5-aza-1-bora-2,8-dioxacyclooctane and mixtures thereof. It should be noted that the methyl, ethyl, propyl, butyl, cyclohexyl, octadecyl, phenyl, steryl, oleyl, coco and tallow moieties may be substituted for the dodecyl moiety in the above heterocyclic compounds.

Metal derivatives of the boron-containing heterocyclic compounds, i.e., metal boramid compounds, herein are conveniently prepared by contacting a boramid compound with a metal, usually in salt form. Thus, the metal acetates, propionates, etc., are suitable for use. The preferred metal compound for use in incorporating the metal ion into the boramid compound is the metal acetate. Generally, the boramid compounds are reacted with the metal compounds in a molar ratio range of from about 1:4 to about 6:1, preferably from about 1:1 to about 4:1, at a pressure of from about atmospheric to about 500 p.s.i.g. and a temperature of from about 176° F. to about 450° F.

Desirable metals are usually selected from transition metals having an atomic number of 21 through 30 or Group IVA metals of the Periodic Table. Transition metals which are suitable for use are selected from scandium, titanium, vanadium, chromium, manganese, iron, cobalt, nickel, copper and zinc and mixtures thereof. Suitable Group IVA metals include lead and tin and mixtures thereof. Normally, the metal will comprise from about 1 to about 17 weight percent, preferably from about 5 to about 9 weight percent of the boramid compound. When a metal is incorporated into the boramid compounds herein, the metal will displace and substitute for the hydrogen atom attached to the oxygen atom which is a component of the hydroxy group attached to the boron atom of the boramid structure.

Representative of the metal boramids are: copper di [-1-oxy-3,7-diphenyl-5-dodecyl-5-aza-1-bora-2, 8-dioxacyclooctane]; copper di [-1-oxy-4,6-diphenyl-5-dodecyl-5-aza-1-bora-2,8-dioxacyclooctane]; copper di [-1-oxy-4,7-diphenyl-5-dodecyl-5-aza-1-bora-2,8-dioxacyclooctane]; copper di [-1-oxy-3,7-dicresyl-5-dodecyl-5-aza-1-bora-2,8-dioxyacyclooctane]; copper di [-1-oxy-4,6-dicresyl-5-dodecyl-5-aza-1-bora-2,8-dioxacyclooctane]; copper di [-1-oxy-4,7-dicresyl-5-dodecyl-5-aza-1-bora-2,8-dioxacyclooctane]; copper di [-1-oxy-3,7-dimethyl-3,7-diphenyl-5-dodecyl-5-aza-1-bora-2,8-dioxacyclooctane]; copper di [-1-oxy-4,6-dimethyl-4,6-diphenyl-5dodecyl-5-aza-1-bora-2,8-dioxacyclooctane]; copper di [-1-oxy-4,7-dimethyl-4,7-diphenyl-5-dodecyl-5-aza-1-bora-2,8-dioxacyclooctane]; copper di [-1-oxy-3,7-para tertiarybutylphenyl -5-dodecyl-5aza-1-bora-2,8-dioxacyclooctane]; copper di [-1-oxy-4,6-para tertiarybutylphenyl-5-dodecyl-5-aza 1-bora-2,8-dioxacyclooctane]; copper di [-1-oxy-4,7-para tertiarybutylphenyl-5-dodecyl-5-aza-1-bora-2,8-dioxacyclooctane]; copper di [-1-oxy-3,7-diphenyl-5-coco-5-aza-1-bora-2,8-dioxacyclooctane]; and copper di[-1-oxy-3,7-diphenyl-5-tallow-5-aza-1-bora-2,8-dioxacyclooctane]and mixtures thereof. Other metals which may be incorporated into the above compounds, i.e., substituted for the copper, include scandium, titanium, vanadium, chromium, manganese, iron, cobalt, nickel, zinc, lead and tin and mixtures thereof. In addition, methyl, ethyl, propyl, butyl, cyclohexyl, octadecyl, phenyl, steryl, oleyl, coco and tallow moieties may be substituted for the dodecyl moiety in the above-described heterocyclic compounds.

Normally, the boron-containing heterocyclic compounds (boramid compounds) or metal derivatives thereof (metal boramids) are blended with a lubricating oil at a concentration of from 0.1 to about 15 weight percent, preferably from 0.5 to about 10 weight percent of the oil composition.

Use of copper and lead in the construction of improved internal combustion engines has created problems in the use of boramid extreme pressure additives in lubricants for such engines, the primary problem being the leaching out of copper and lead from bearings used in said engines.

Copper corrosion in engine bearings is inhibited by adding to the lubrication composition a corrosion inhibiting amount, normally from 0.001 to about 5 weight percent, preferably from 0.005 to about 2.5 weight percent of a hydrocarbon polysulfide derivative of 2,5-dimercapto-1,3,4-thiadiazole having the formula:

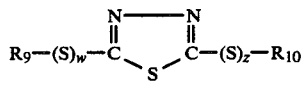

wherein $R_9$ and $R_{10}$ are the same or different moieties selected from hydrogen or straight or branched chain alkyl, cyclic or alicyclic alkyl, aryl, alkylaryl or arylalkyl radicals having from 2 to about 30 carbon atoms, and w and z are integers between 1 and 8. It should be noted that $R_9$ and $R_{10}$ cannot both be hydrogen because the compound would be rendered insoluble in lubricating oils. Thus, when $R_9$ is hydrogen, $R_{10}$ must be selected from one of the other moieties described above, and vice versa.

The herein-described polysulfide derivatives of 2,5-dimercapto-1,3,4-thiadiazole can be suitably prepared by several methods. For example, they can be prepared by reacting 2,5-dimercapto-1,3,4-thiadiazole with a suitable sulfenyl chloride, or by reacting the dimercaptan with chlorine and reacting the resultant disulfenyl chloride below,

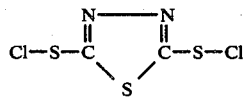

with a primary or tertiary mercaptan. Bis-trisulfide derivatives are obtained by reacting the dimercaptan with a mercaptan and a sulfur chloride in molar ratios of from 1:2:2 to 1:2:4 at a temperature of from about 120° to 212° F. Higher polysulfides may be prepared by reacting the thiadiazole di- or trisulfides with sulfur at temperatures of about 200° F. to 400° F. Another method of preparing the polysulfides of the present invention involves reacting 2,5-dimercapto-1,3,4-thiadiazole with a mercaptan and sulfur in the molar ratio of from 1:1:1 to 1:4:16 at temperatures of from about 160° F. to about 300° F. The 2-mercapto, 5 alkyldithio-1,3,4-thiadiazole derivative may be prepared by reacting less than the stoichiometric amount of a primary or tertiary mercaptan with the disulfenyl chloride above to produce the bis form of the compound.

Compounds produced in accordance with the above procedure preferably are polysulfides of 1,3,4-thiadiazole-2,5-bis(alkyl, di, tri or tetra sulfide) containing from 2 to about 30 carbon atoms. Desirable polysulfides include 1,3,4-thiadiazole-2,5-bis (octyldisulfide); 1,3,4-thiadiazole-2,5 bis(octytrisulfide); 1,3,4-thiadiazole-2,5 bis (octyltetrasulfide); 1,3,4-thiadiazole-2,5 bis (dodecyldisulfide); 1,3,4-thiadiazole-2,5 bis (dodecyltrisulfide); 1,3,4-thiadiazole-2,5 bis (dodecyltetrasulfide); 2-lauryldithia-5-thiaalphamethylstyryl-1,3,4 thiadiazole; 2-lauryltrithia-5-thiaalphamethylstyryl-1,3,4 thiadiazole; 2-mercapto-5-octyldithio-1,3,4-thiadiazole and 2-mercapto-5-dodecyldithio-1,3,4-thiadiazole and mixtures thereof.

An especially desirable ratio of the above copper corrosion inhibitors, when two are mixed together is from 1:20 to 20:1, preferably from 1:10 to 10:1.

A small but effective amount of terephthalic acid is the preferred lead corrosion inhibitor herein. The terephthalic acid may be prepared in accordance with conventional techniques and apparatus. For example, para-xylene may be oxidized to terephthalic acid at increased temperature and pressure in the presence of acetic acid, a bromine promoter and a heavy metal catalyst, i.e., cobalt, manganese, etc. A second method of preparing terephthalic acid comprises reacting benzene and potassium carbonate over a cadmium catalyst at increased temperature and pressure. Generally, the terephthalic acid is incorporated into lubricating oils at a concentration of from about 0.001 to about 1 weight percent, especially from about 0.01 to about 0.05 weight percent.

The oxidation inhibitors or anti-oxidants herein have high enough molecular weights to ensure that they remain stable in a hot crankcase oil, e.g. 300° F. and, in addition, enhance the corrosion preventive properties of the copper and lead corrosion inhibitors by interrupting or terminating the attack of oxidants upon copper/lead-bearing metal. One type of corrosion is an oxidative process involving the loss of electrons from the corroding metal by an oxidant such as oxygen, air, nitrogen oxides, partially burned gasoline, blow-by products and the like. The oxidation inhibitors as described hereinafter are selected from the group consisting of bis(dithiobenzil) metal derivatives and sulfur bridged, bis hindered phenols and mixtures thereof. These compounds effectively limit or prevent the attack of oxidants on copper/lead metal. In addition, these compounds also help to control oil oxidation as manifested by reduced sludge and varnish formation, and by reduced oil thickening.

The bis(dithiobenzil) metal derivatives herein preferably have the formula:

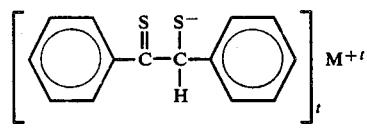

wherein M is a first row transition metal and t is an integer between 1 and 4. Suitable transition metals include vanadium, chromium, manganese, iron, cobalt, nickel, copper, zinc, preferably iron, cobalt and nickel.

Generally, the bis(dithiobenzil) metal derivatives are prepared in accordance with conventional techniques and procedures. For example, benzoin is reacted with phosphorus sulfide in the presence of dioxane at increased temperature to produce the thiophosphoric ester of dithiobenzoin. The desired divalent metal, for example, metallic halide, is reacted with the above-described thiphosphoric ester of dithiobenzoin to produce the bis(dithiobenzil) metal derivative.

It should be noted that the bis(dithiobenzil) metal derivatives herein do not readily dissolve in lubricant compositions. However, when the bis(dithiobenzil) metal derivatives are mixed with the boramid compounds herein, especially dodecylamino di(phenylethylate) hydrogen borate, the mixture goes into solution in lubricant compositions such as motor oils. Although the invention is not bound by any theory, it is believed that the boramid compound and bis(dithiobenzil) metal derivative form a complex which renders the bis(dithiobenzil) metal derivative soluble in lubricants, for example, motor oil.

The sulfur bridged, bis hindered phenols herein preferably have the formula:

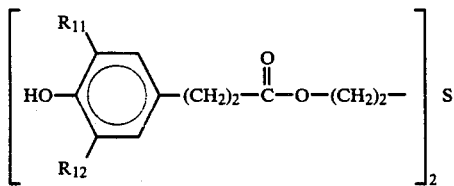

wherein $R_{11}$ and $R_{12}$ are selected from the same or different alkyl groups having from 1 to 6 carbon atoms.

In general, the sulfur bridged, bis hindered phenols are prepared by conventional esterification procedures using a suitable alcohol and an acid of the formula:

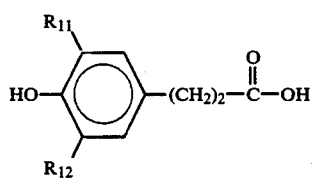

or an acid halide, acid anhydride or mixed anhydride thereof, and wherein $R_{11}$ and $R_{12}$ are as described before. The suitable alcohol herein preferably is thiodiglycol having the formula $(HOCH_2CH_2)_2S$ which is prepared by the hydrolysis of dichloroethyl sulfide or the interaction of ethylene chlorohydrin and sodium sulfide using conventional techniques and procedures.

Sulfur bridged, bis hindered phenols which are suitable for use as anti-oxidants include thiodiethyl bis-(3,5-di-methyl-4-hydroxy) hydrocinnamate; thiodiethyl bis-(3,5-di-ethyl-4-) hydrocinnamate; thiodiethyl bis-(3,5-di-propyl-4-hydroxy) hydrocinnamate; thiodiethyl bis-(3,5-di-butyl-4-hydroxy) hydrocinnamate; thiodiethyl bis-(3,5-di-pentyl-4-hydroxy) hydrocinnamate and thiodiethyl bis-(3,5-di-hexyl-4-hydroxy) hydrocinnamate and mixtures thereof.

Generally, the anti-oxidants herein are incorporated into lubricant compositions at concentrations of from 0.01 to about 1 weight percent, preferably from 0.025 to about 0.10 weight percent.

The extreme pressure, anti-wear, friction reducing, corrosion inhibition and anti-oxidation additives described herein may be incorporated in a wide variety of lubricating oils, for example, mineral oil, (including automobile engine oil), synthetic oil, industrial oils, for example, cutting oil, metal working fluids and grease. In addition, the additives may be added to lubricating oils derived from paraffins, naphthenic or mixed base crude petroleum oils, that have been subjected to solvent and/or sulfuric-acid treatment, aluminum chloride treatment, hydrogenation and/or other refining treatments. In addition, the additives described herein may be incorporated in petroleum distillates, such as diesel fuel, jet engine fuel, furnace oil, gas oil and other light oils.

Preferred distillate lubrication oils which are improved by the addition of the additives herein have an initial boiling point within the range of 350° F. to about 475° F., an end point in the range of about 500° F. to about 1,100° F., and a flash point not lower than 110° F.

Lubricants derived from oil shale are particularly desirable for use herein. Oil shale is broadly defined as a variety of compact sedimentary rock, generally laminated, that contains little or no oil but does contain organic material, derived from aquatic organisms or waxy spores and pollen grains, which is convertible to oil by heat. Crude shale oil, in combination with water, gas and spent shale containing a carbonaceous residue and mineral matter, is formed by the pyrolysis of oil shale. The hydrocarbons of shale oil are highly unsaturated, resembling the products of thermal cracking of petroleum, as would be expected because of the pyrolytic origin of shale oil. Once the shale oil is extracted, it is subjected to conventional hydrotreating procedures to produce a variety of hydrocarbon products, including lubricants.

Synthetic lubricating oils useful herein are those oils derived from a product of chemical synthesis (man-made oils). Typical examples of such compositions include the polyglycol fluids (i.e., polyalkylene glycol); silicones which consist of a silicone-oxygen polymer chain to which are attached hydrocarbon branches composed of either alkyl or phenyl groups; phosphates; polyphenyl esters; synthetic hydrocarbons and various esters of organic acids and alcohols.

The polyalkylene glycol lubricating oils suitable for use herein preferably are derived from the reaction product of the appropriate alkylene oxides. The alkylene moiety of the above compositions have a carbon chain of from about 1 to about 10 carbon atoms, preferably from about 200 to about 1,000, most preferably from about 200 to about 800. Representative examples of suitable polyalkylene glycols include, polyethylene glycol, polypropylene glycol, polyisopropylene glycol, polybutylene glycol and the like.

Synthetic lubricating oils derived from hydrocarbons are generally of two types, namely, dialkylated benzene and polymerized alpha-olefins. Dialkylated benzene herein is formed from the condensation product of the appropriate alkyl compound and has a carbon chain from about 5 to about 50 carbon atoms, preferably from about 8 to about 20 carbon atoms; and a molecular weight of from about 200 to about 1,500, preferably from about 300 to about 700. Representative compounds include di-n-decylbenzene, n-decyln-tetradecylbenzene, and n-nonyl-n-dodecylbenzene.

Alpha-olefins suitable for use in preparing lubricating oils herein are characterized by the formula $RCH=CH_2$ wherein R is a radical selected from the group of hydrogen and alkyl radicals having from about 4 to about 18 carbon atoms, preferably from about 6 to about 10 carbon atoms, and having a molecular weight of from about 80 to about 300, preferably from about 100 to about 200. Typical compounds include 1-octene, 1-decene and 1-dodecene.

Phosphates suitable for use herein as synthetic lubricating oils are the phosphate esters having the formula $O=P(OR)_3$, wherein R is aryl or alkyl having from about 4 to about 20 carbon atoms, preferably from 6 to about 10 carbon atoms, and have a molecular weight within the range of from about 200 to about 1,000, preferably from about 300 to about 550. Representative compounds include trioctyl phosphate, tricresyl phosphate and dicresyl methyl phosphate.

Esters of organic acids which are suitable for use herein as synthetic lubricating oils preferably are selected from organic acids having carbon chains of from $C_4$ to $C_{40}$ carbon units. Organic acids which may be reacted with the alcohols herein include caproic, decanoic, sebacic, laurel, oleic, stearic, palmitic, etc. Likewise, alcohols herein may be derived from either natural or synthetic origin, for example, pentaerythritol, trimethylolpropane, amyl, 2-ethyl-hexanol or laurel alcohol, may be used to form the desired ester. The esters are formed using conventional methods. For example, the esters may be prepared by reaction of the desired alcohol with the desired acid, acid anhydride or acid halide using conventional reaction conditions and techniques.

If desired, the additives described herein may be employed in conjunction with other additives commonly used in petroleum products. Thus, there may be added to the oil compositions of this invention rust inhibitors, emulsifying agents, dyes, haze inhibitors, anti-static agents, detergents, dispersants, viscosity index improvement agents, pour point reducing agents, other extreme pressure additives, corrosion inhibitors and oxidation inhibitors. Soaps or other thickening agents may be added to the lubricating oil compositions to form compositions having the consistency of a grease. When other additives are employed, it may be desirable, although not necessary to prepare additive concentrates comprising concentrated solutions of the herein boron or metal-boron derivatives together with said other additives whereby the several additives are added simultaneously. Dissolution of the additive or additive concentrate into the oil composition may be facilitated by mixing accompanied with mild heating, but this is not absolutely essential.

The invention will be further described with reference to the following examples.

EXAMPLE I

The boramid compound, 1-hydroxy-3,7-diphenyl-5-coco-5-aza-1-bora-2,8-dioxacyclooctane, is prepared by adding 14,889 grams of cocoamine[1] and 17,516 grams of styrene oxide to a 65 liter round bottomed flask that contains 13 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 34,373 grams of 1-hydroxy-3,7-diphenyl-5-coco-5-aza-1-bora-2,8-dioxacyclooctane.

[1] Cocoamine is a mixture of primary amines consisting of approximately 52 percent dodecylamine, 19 percent of tetradecylamine, 9 percent of hexadecyl amine, 6.5 percent of octylamine, 6 percent of decylamine, 2 percent of octadecyl amine and 5 percent of a mixture of octadecenylamine and octadecadienylamine. Cocoamine is marketed commercially by the Armak Company under the trademark of Armeen CD.

EXAMPLE II

A boramid compound is prepared by adding 17,605 grams of tallowamine[2] and 15,362 grams of styrene oxide to a 65 liter round bottomed flask that contains 11.34 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product at a temperature of 400° F. The reaction produces 34,695 grams of 1-hydroxy-3,7-diphenyl-5-tallow-5-aza-1-bora-2,8-dioxacyclooctane.

[2] Tallowamine is a mixture of amines consisting of approximately 29 percent hexadecylamine, 20.5 percent octadecylamine, 44 percent of a mixture of octadecenylamine and octadecadienylamine, 3 percent tetradecylamine, 1.5 percent hexadecenylamine, 1 percent heptadecylamine and 0.5 percent tetradecenylamine. Tallowamine is marketed commercially by the Armak Company under the trademark Armeen T.

EXAMPLE III

The boramid compound, 1-hydroxy-3,7-diphenyl-5-dodecyl-5-aza-1-bora-2,8-dioxacyclooctane, is prepared by adding 13,502 grams of dodecylamine and 17,516 grams of styrene oxide to a 65 liter round bottomed flask that contains 13.34 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 32,986 grams of 1-hydroxy-3,7-diphenyl-5-dodecyl-5-aza-1-bora-2,8-dioxacyclooctane.

EXAMPLE IV

The boramid compound, 1-hydroxy-4,6-dicresyl-5-dodecyl-5-aza-1-bora-2,8-dioxacyclooctane is prepared by adding 61.7 grams of dodecylamine, 89.3 grams of para methylstyrene oxide and 250 ml of toluene to a single necked one liter round-bottomed flask. The toluene acts as a solvent and as an azeotrope for water produced during the reaction. The mixture thus formed is heated until it begins to reflux. Next, the mantle heat is adjusted to give a moderate reflux rate. The reaction mixture is refluxed for 24 hours. The reaction mixture is cooled to room temperature and 21 grams of boric acid are added to the flask. Next, the flask is equipped with a Dean-Stark trap topped with a water-cooled condenser and the reaction mixture is refluxed until water stops collecting in the trap (12 ml). Toluene is distilled from the reaction product. The reaction produces 160 grams of product.

EXAMPLE V

The boramid compound, 1-hydroxy-3,7-dimethyl-3,7-diphenyl-5-dodecyl-5-aza-1-bora-2,8-dioxacyclooctane, is prepared by following the procedure of Example III with the following substitution:

Alpha methyl styrene oxide is substituted for the styrene oxide with substantially the same results.

EXAMPLE VI

Boric acid (21 grams), para tertiary-butyl styrene oxide (119.3 grams), dodecylamine (61.7 grams) and 250 ml of toluene are mixed in a one liter single-necked flask to prepare 1-hydroxy-4,6-para tertiarybutylphenyl-5-dodecyl-5-aza-1-bora-2,8-dioxacyclooctane in accordance with the procedure of Example IV. The flask is equipped with a heating mantle, Dean-Stark trap and water-cooled condenser. The mixture is heated under reflux until the reaction is completed; (12 ml) of water collects in the Dean-Stark trap. Next, toluene is distilled from the reaction mixture. The product thus prepared is suitable for use as an extreme pressure, anti-wear and friction reducing additive for lubricating compositions.

It should be noted that the other primary amines herein may be substituted for the dodecylamine above, to form the corresponding boramid compound.

EXAMPLE VII

A copper derivative of 1-hydroxy-3,7-diphenyl-5-coco-5-aza-1-bora-2,8-dioxacyclooctane is prepared by following the procedure of Example I with the following exception: the above-described compound (47 grams), 100 ml of toluene, 20 ml of triethyl amine and 10 grams of cupric acetate are mixed in a single-necked, 500 ml round bottom flask, equipped with a heating mantle, Dean-Stark trap and water-cooled condenser. The mixture is refluxed for 16 hours, then filtered and the toluene, amine, water and acetic acid (produced in situ) are distilled from the reaction product. Using the above-procedure, copper di[-1-oxy-3,7-diphenyl-5-dodecyl-5-aza-1-bora-2,8-dioxacyclooctane] is produced.

It is to be noted that other transition metals having an atomic number from 21 to 30, and Group IVA metals of the periodic table may be substituted for the copper metal herein to prepare corresponding metal derivatives of the above compound.

EXAMPLE VIII

A nickel derivative of 1-hydroxy-4,6-diphenyl-5-coco-5-aza-1-bora-2,8-dioxacyclooctane is prepared by following the procedure of Example VII with the following exception: nickel acetate is substituted for the cupric acetate. The reaction produces nickel di[-1-oxy-3,7-diphenyl-5-coco-5-aza-1-bora-2,8-dioxacyclooctane].

EXAMPLE IX

Lead di[-1-oxy-3,7-diphenyl-5-coco-5-aza-1-bora-2,8-dioxacyclooctane] is prepared in accordance with the procedure of Example I with the following exception:

The reaction product produced in Example I (23.5 grams), 100 ml of toluene, 9.5 grams of lead acetate and 100 ml of triethylamine are mixed in a single-necked 500 ml round bottom flask, equipped with a water-cooled condenser and heating mantle and Dean-Stark trap. The mantle heat is adjusted until a moderate rate of reflux is obtained. The mixture thus formed is refluxed for 18 hours. Next, the mixture is filtered, toluene, water, triethylamine and acetic acid (produced in the reaction) are distilled from the reaction product. The reaction produces lead di[-1-oxy-3, 7-diphenyl-5-dodecyl-5-bora-2,8-dioxacyclooctane.

EXAMPLE X

Iron di[-1-oxy-3, 7-diphenyl-5-coco-5-aza-1-bora-2, 8-dioxyacyclooctane is prepared according to the procedure of Example I with the following exception:

a mixture comprising 23.5 grams of the reaction product produced in Example I, 100 ml of toluene, 4.3 grams of ferrous acetate and 100 ml of triethylamine are introduced into a single-necked 500 ml round bottom flask, equipped with Dean-Stark trap, water-cooled condenser and heating mantle. The heating mantle is adjusted to give a moderate rate of reflux of the reaction mixture. The mixture is refluxed for 18 hours. Next, the mixture is filtered and the triethylamine, toluene, and acetic acid (produced in the reaction) are distilled from the reaction product.

EXAMPLE XI

A boramid compound is prepared by adding 17,093 grams of octadecylamine and 15,362 grams of styrene oxide to a 65 liter round bottomed flask that contains 13 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product at a temperature of 400° F. The reaction produces 34,183 grams of 1-hydroxy-3,7-diphenyl-5-octadecyl-5-aza-1-bora-2,8-dioxacyclooctane.

EXAMPLE XII

The procedure of Example XI is followed to produce 1-hydroxy-3,7-diphenyl-5-phenyl-5-aza-1-bora-2,8-dioxacyclooctane with the following exception:

Phenylamine is substituted for octadecylamine.

EXAMPLE XIII

Zinc di[-1-oxy-3,7-diphenyl-5-coco-5-aza-1-bora-2,8-dioxacyclooctane] is produced according to the procedure of Example VII except that zinc acetate is substituted for the cupric acetate.

EXAMPLE XIV

Tin di[-1-oxy-3,7-diphenyl-5-coco-5-aza-1-bora-2, 8-dioxacyclooctane] is prepared by substituting tin acetate for the cupric acetate in Example VII.

EXAMPLE XV

Lead di[-1-oxy-4,6-diphenyl-5-dodecyl-5-aza-1-bora-2, 8-dioxacyclooctane] is prepared in accordance with the procedure of Example III with the following exception:

The reaction product produced in Example III (23.95 grams), 100 ml of toluene, 9.5 grams of lead acetate and 100 ml of triethylamine are mixed in a single-necked 500 ml round bottom flask, equipped with a water-cooled condenser, heating mantle and Dean-Stark trap. The mantle heat is adjusted until a moderate rate of reflux is obtained. The mixture thus formed is refluxed for 18 hours. Next, the mixture is filtered and the toluene, triethylamine, water and acetic acid (produced in-situ) are distilled from the reaction product. The reaction produces lead di[-1-oxy-3,7-dimethyl-3,7-diphenyl-5-dodecyl-5-aza-1-bora-2,8-dioxacyclooctane].

EXAMPLE XVI

A nickel derivative of 1-hydroxy-4, 6-dicresyl-5-dodecyl-5-aza-1-bora-2, 8-dioxacyclooctane is prepared by following the procedure of Example XV with the following exception:

parametyl styrene oxide is substituted for styrene oxide and nickel acetate is substituted for lead acetate. The reaction produces nickel di[-1-oxy-3,7-dicresyl-5-dodecyl-5-aza-1-bora-2,8-dioxacyclooctane].

EXAMPLE XVII

Iron di[-1-oxy-3,7-diparatertiarybutyl-phenyl-5-dodecyl-5-aza-1-bora-2,8-dioxacyclooctane] is prepared according to the procedure of Example VI with the following exception:

a mixture comprising 28.4 grams of the reaction product produced in Example VI, 100 ml of toluene, 4.3 grams of ferrous acetate and 100 ml of triethylamine are introduced into a single-necked 500 ml round bottom flask, equipped with Dean-Stark trap, water-cooled condenser and heating mantle. The heating mantle is adjusted to give a moderate rate of reflux of the reaction mixture. The mixture is refluxed for 18 hours, filtered, and the toluene, triethylamine, water and acetic acid (produced in-situ) are distilled from the reaction product.

EXAMPLE XVIII

Zinc di[-1-oxy-3,7-diphenyl-5-dodecyl-5-aza-1-bora-2,8-dioxacyclooctane] is produced according to the procedure of Example XV except that zinc acetate is substituted for lead acetate.

EXAMPLE XIX

Tin di[-1-oxy-3,7-diphenyl-5-dodecyl-5aza-1-bora-2,8-dioxacyclooctane] is prepared by substituting tin acetate for lead acetate in Example XV.

EXAMPLES XX to XXVI

Extreme pressure, anti-wear and friction reducing additives produced according to the procedure of Examples I, VII, IX, X, XIII, and XIV are mixed with separate portions of 450 neutral oil at concentrations of 2 weight percent.

Each lubricant composition is tested in accordance with the procedure disclosed in ASTM:D3233-73 (Reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. A summary of the results obtained is disclosed in Table 1 below:

TABLE 1

| | TORQUE ON JOURNAL (LBS.-IN) | | | | | | |
|---|---|---|---|---|---|---|---|
| | | Example | | | | | |
| True Load lbs | XX (450 Neutral Oil) | XXI Oil With Additive of Ex. I | XXII Oil With Additive of Ex. VII | XXIII Oil With Additive of Ex. IX | XXIV Oil With Additive of Ex. X | XXV Oil With Additive of Ex. XIII | XXVI Oil With Additive of Ex. XIV |
| 300 | 9 | 7 | 11 | 9 | 10 | 9 | 7 |
| 500 | 12 | 9 | 15 | 15 | 15 | 14 | 9 |
| 750 | Journal Shear | 17 | 21 | 21 | 22 | 22 | 16 |
| 990 | — | — | — | — | — | Journal Shear | — |
| 1,000 | — | 24 | 28 | 30 | 28 | — | 19 |
| 1,050 | — | — | Journal Shear | Journal Shear | Journal Shear | — | 23 |
| 1,250 | — | Journal Shear | — | — | — | — | 26 |
| 1,500 | — | — | — | — | — | — | Journal Shear |
| 1,750 | | | | | | | |

The above data indicate that the boron containing heterocyclic compounds described above impart extreme pressure properties to 450 neutral oil at concentrations of 2 weight percent.

EXAMPLES XXVII and XXVIII

The extreme pressure, anti-wear and friction reducing additive produced in accordance with the procedure of Example I is mixed at a concentration of 2 weight percent with SAE 30 motor oil which contains 0.05 weight percent phosphorus. A sample of the SAE 30 motor oil which does not contain the additive of Example I is used as a control.

Each lubricant composition is tested in accordance with the procedure disclosed in ASTM D3233-73 (Reapproved 1978) using a Falex lubricant tester. A summary of the results is disclosed in Table 2 below.

TABLE 2

| | TORQUE ON JOURNAL (LBS.-IN.) | |
|---|---|---|
| | Example | |
| True Load Lbs. | XXIV Control (SAE 30 Motor Oil) | XXV SAE 30 Motor Oil With Additive of Ex. I |
| 300 | 9 | 8 |
| 500 | 14 | 12 |
| 750 | 20 | 17 |
| 950 | Journal Shear | — |
| 1,000 | — | 22 |
| 1,250 | — | 28 |
| 1,400 | — | Journal Shear |

The extreme pressure property of SAE 30 motor oil is substantially enhanced in Table 2 above when 2 weight percent of 1-hydroxy-3,7-diphenyl-5-coco-5-azo-1-bora-2,8-dioxacyclooctane is added to said SAE motor oil.

EXAMPLE XXIX

The copper corrosion inhibitor, 1,3,4-thiadiazole-2,5-bis(dodecyldisulfide), is prepared by chlorinating 284 grams of n-dodecyl mercaptan in 0.6 liter of carbon tetrachloride with 1.47 moles of chlorine over a two hour period at a temperature of about 23° F. to about 32° F. Next, sulfenyl chloride which forms as a reaction product is stripped with nitrogen to remove hydrogen chloride, and the resultant compound is added to 86 grams of a 2,5-dimercapto-1,3,4-thiadiazole slurry. The mixture is heated at 86° F. for 1½ hours and the resultant compound (1,3,4-thiadiazole-2,5-bis (dodecyldisulfide) is recovered by washing with water and sodium bicarbonate and vacuum stripping to remove carbon tetrachloride.

EXAMPLE XXX

The procedure of Example XXIX is followed to prepare 1,3,4-thiadiazole-2,5-bis (octyldisulfide) with the following exception: octyl mercaptan is substituted for the dodecylmercaptan.

EXAMPLE XXXI

The oxidation inhibitor, bis(dithiobenzil) iron (II) is prepared by adding 400 grams of benzoin and 600 grams of phosphorus sulfide to a single-necked 5 liter, round bottom flask equipped with heating mantle and water-cooled condenser and containing 1,500 ml of dioxane. The mixture thus formed is refluxed for two hours. Next, 200 grams of hydrated ferrous chloride dissolved in 500 ml of water is added to the 5 liter flask and the mixture is heated on a steam bath (212° F.) for 2 hours. The reaction product thus formed (169.5 grams) is filtered and washed with methanol.

EXAMPLE XXXII

The oxidation inhibitor, bis(dithiobenzil) nickel is prepared by adding a mixture of 100 grams of benzoin, 150 grams of phosphorus sulfide and 700 ml of dioxane to a 5 liter, single necked flask equipped with heating mantle and water cooled condenser. The above-described mixture is, then, refluxed for 2 hours, during which the thiophosphoric ester of dithiobenzoin is formed and hydrogen sulfide is evolved. The reaction mixture is cooled and a solution of 50 grams of nickel chloride (hydrated) in 200 ml of water is added to the flask and heated (212° F.) for 2 hours on a steam btah. Black crystals of bis(dithiobenzil) nickel are formed and collected by filtering the cooled solution. Purification is effected by extraction with boiling toluene.

It should be noted that other bis(dithiobenzil) metal derivatives may be prepared in accordance with the above procedure by substituting transition metals or Group IVA metals as described herein for the nickel described above.

EXAMPLE XXXIII

The oxidation inhibitor, thiodiethyl bis-(3,5-di-t-butyl-4-hydroxy) hydrocinnamate is prepared by melting together 17.95 weight percent of B.B'-dihydroxy-diethyl sulfide, 81.41 weight percent of (3,5-di-t-butyl-4-hydroxy) hydrocinnamate acid and 0.64 weight percent of sodium methylate under a nitrogen atmosphere at 266° F. for two and one-half hours. Methanol thus formed is separated from the reaction mixture and condensed in a dry-ice trap using nitrogen gas as a carrier. The reactants are heated at 149° F. for three hours and the reaction product is dissolved in warm benzene, filtered and the benzene filtrate is washed three times with saturated sodium chloride solution. The filtrate is, next, dried over anhydrous sodium sulfate and the solvent evaporated using convention techniques Thiodiethyl bis-(3,5-di-t-butyl-4-hydroxy) hydrocinnamate is isolated and purified by successive recrystallization from hexane and a mixture of hexane and t-butanol.

EXAMPLE XXXIV TO XXXIX

Lubricant compositions as described in Table 4 below are tested for copper and lead corrosion inhibition using a single-cylinder Labeco CLR Test Engine equipped with sintered copper (65 wt %) /lead (35 wt. %) connecting rod bearings, in accordance with the procedure of Federal Test Method Standard No. 791B, Method 3405.2. The lubricant compositions used are a standard SAE 30 motor oil containing the additives and concentrations disclosed in Table 4 below.

The copper-lead corrosion tests are conducted in accordance with the test conditions of Table 3 below:

TABLE 3

| Operating Conditions | |
|---|---|
| Test Duration, Hours | 40 |
| Speed, RPM | 3150 ± 25 |
| Load, BHP | 6.5a |
| Fuel Flow, Lb/Hr. | 4.75 ± 0.25 |
| Air/Fuel Ratio | 14.0 ± 0.5 |
| Jacket Outlet Coolant Temp., °F. | 200 ± 2 |
| Gallery Oil Temp., °F. | 290 ± 2 |
| Spark Advance, BTDC | 35 ± 1 |
| Oil Pressure, PSI | 40 ± 2 |
| Crankcase Vacuum in. $H_2O$ | 2 ± 0.5 |
| Exhaust Back Pressure, in. Hg. | 0.5 ± 0.5 |
| Crankcase Off-Gas, CFH | 30 ± 1 |
| Oil Charge, Pints | 3.5 |

The test is conducted by charging 3.5 pints of the test lubricant to the engine sump. Test duration consists of 40 hours operation at the prescribed test conditions of Table 2 above. When the prescribed gallery oil temperature is reached, the test time begins. Interim oil adjustments are made at the end of 10, 20 and 30 hours of test operation. A copper/lead bearing weight loss of about 40 mg or lower is considered acceptable. All of the tests are conducted using SAE 30 motor oil containing the additives and/or compounds, including concentrations in Table 4 below.

TABLE 4

| Example | Compound of Example I (Wt. %) | Copper Corrosion Inhibitor (B) (Wt. %) | Terephthalic Acid (Wt. %) | Anti-Oxidant (Wt. %) | Phosphorous (Wt. %) | Amoco (E) PCO-059 | CRC L-30 Engine Test 40 hours (BWL, mg) (F) |
|---|---|---|---|---|---|---|---|
| XXXIV | 2.12 | — | — | — | 0.05 | 6.5 | 93 |
| XXXV | 2.12 | 0.050 | 0.05 | — | 0.05 | 6.5 | 43.0 |
| XXXVI | 2.12 | 0.075 | 0.05 | — | 0.05 | 6.5 | 40.0 |
| XXXVII | 2.00 | 0.03 | 0.03 | — | 0.05 | 6.5 | 38 |
| XXXVIII | 2.00 | 0.075 | 0.05 | 0.05 (C) | 0.05 | 6.5 | 34.8 |

TABLE 4-continued

| Example | Compound of Example I (Wt. %) | Copper Corrosion Inhibitor (B) (Wt. %) | Terephthalic Acid (Wt. %) | Anti-Oxidant (Wt. %) | Phosphorous (Wt. %) | Amoco (E) PCO-059 | CRC L-30 Engine Test 40 hours (BWL, mg) (F) |
|---------|-------------------------------|----------------------------------------|---------------------------|-----------------------|---------------------|-------------------|---------------------------------------------|
| XXXIX   | 2.12                          | 0.075                                  | 0.05                      | 0.05 (D)              | 0.05                | 6.5               | 26.4                                        |

(A) 1-hydroxy-3,7-diphenyl-5-coco-5-aza-1-bora-2,8-dioxacyclooctane.
(B) Copper Corrosion Inhibitor = A mixture of 83 weight percent 1,3,4-thiodiazole-2,5-bis(octyldisulfide) and 17 weight percent of 2 mercapto-5 octyldithio-1,3,4-thiadiazole, marketed by the Amoco Oil Company under the Trademark of Amoco 150.
(C) Anti-oxidant = bis(dithiobenzil) iron.
(D) Anti-oxidant = thiodiethyl bis(3,5-di-t-butyl-4-hydroxy) hydrocinnamate.
(E) Amoco PCO-059 = detergent/dispersant package marketed commercially by the Amoco Oil Company.
(F) BWL = bearing weight loss.

As can readily be determined from the above Examples, the lubricant additives herein impart extreme pressure, anti-wear friction reducing, copper and lead corrosion inhibition and antioxidant properties to lubricant compositions when used in accordance with the disclosure herein In particular, it is noted that the lubricating composition prepared in accordance with the invention, i.e., Examples XXXVIII and XXXIX, provided especially useful results.

Obviously, many modifications and variations of the invention, as hereinbefore set forth, may be made without departing from the spirit and scope thereof, and therefore only such limitations should be imposed as are indicated in the appended claims.

We claim:

1. A lubricating composition comprising a major amount of a lubricating oil and a minor amount of:
    (A) an extreme pressure, anti-wear and friction reducing additive of the formula:

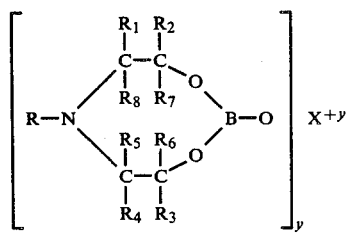

where R is hydrogen or an alkyl, alkene, alkadiene, aryl, alkylaryl or arylalkyl radical having from 1 to about 24 carbon atoms, $R_1$, $R_2$, $R_3$ and $R_4$ are the same or different radicals selected from hydrogen or alkyl, aryl, alkylaryl or arylalkyl radicals having from 1 to about 30 carbon atoms, wherein at least one of said $R_1$, $R_2$, $R_3$ or $R_4$ is an aryl, alkylaryl or arylalkyl radical having from about 6 to about carbon atoms, $R_5$, $R_6$, $R_7$ and $R_8$ are the same or different radicals selected from hydrogen or an alkyl radical having from 1 to about 6 carbon atoms, Y is an integer between 1 and 4, and X is hydrogen or a metal selected from a transition metal having an atomic number of 21 through 30 or a Group IVA metal;
    (B) A copper corrosion inhibitor comprising a compound having the formula:

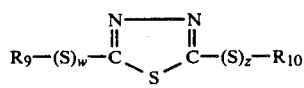

wherein $R_9$ and $R_{10}$ are the same or different moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different integers between 1 and 8;
    (C) A lead corrosion inhibitor comprising terephthalic acid; and
    (D) An oxidation inhibitor comprising: a metal additive having the formula:

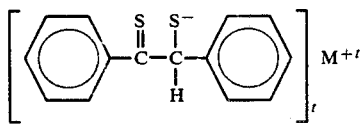

wherein M is a first row transition metal and t is an integer between 1 and 4.

2. The lubricating composition defined in claim 1 wherein the extreme pressure, anti-wear and friction reducing additive is a member selected from the group consisting of 1-hydroxy-3,7-diphenyl-5-dodecyl-5-aza-1-bora-2,8-dioxacyclo-octane; 1-hydroxy-4,6-diphenyl-5-dodecyl-5-aza-1-bora-2, 8-dioxacyclooctane; 1-hydroxy-4,7-diphenyl-5-dodecyl-5-aza-1-bora-2,8-dioxacyclooctane; 1-hydroxy-3,7-dicresyl-5-dodecyl-5-aza-1-bora-2,8-dioxacylclooctane; 1-hydroxy-4,6-dicresyl-5-dodecyl-5-aza-1-bora-2,8-dioxacyclooctane; 1-hydroxy-4,7-dicresyl-5-dodecyl-5-aza-1-bora-2,8-dioxacyclooctane, 1-hydroxy-3,7-dimethyl-3,7-diphenyl-5-dodecyl-5-aza-1-bora-2, 8-dioxacyclooctane; 1-hydroxy-4,6-dimethyl-4,6-diphenyl-5-dodecyl-5-aza-1-bora-2,8-dioxacyclooctane; 1-hydroxy-4,7-dimethyl-4,7-diphenyl-5-dodecyl-5-aza-1-bora-2, 8-dioxacyclooctane; 1-hydroxy-3,7-para tertiarybutylphenyl-5-dodecyl-5-aza-1-bora-2,8-dioxacyclooctane; 1-hydroxy-4, 6-para tertiarybutylphenyl-5-dodecyl-5-aza-1-bora-2, 8-dioxacyclooctane; 1-hydroxy-4, 7-para tertiarybutylphenyl-5-dodecyl-5-aza-1-bora-2,8-dioxacyclooctane; 1-hydroxy-4,6-diphenyl-5-coco-5-aza-1-bora-2,8-dioxacyclooctance; 1-hydroxy-4,7-diphenyl-5-coco-5-aza-1-bora-2,8-dioxacyclooctane; 1-hydroxy-4,6-diphenyl-5-tallow-5-aza-1-bora-2,8-dioxacyclooctane; 1-hydroxy-4,7-diphenyl-5-tallow-5-aza-1-bora-2,8-dioxacyclooctane and 1-hydroxy-3,7-diphenyl-5-coco-5-aza-7-diphenyl-5-tallow-5-aza-1-bora-2,8-dioxacyclooctane and mixtures thereof.

3. The lubricating composition defined in claim 1 wherein the extreme pressure, anti-wear and friction reducing additive is a member selected from the group consisting of metal derivatives of 1-hydroxy-3,7-diphenyl-5-dodecyl-5-aza-1-bora-2,8-dioxacyclo-octane; 1-hydroxy-4,6-diphenyl-5-dodecyl-5-aza-1-bora-2,8-dioxacyclooctane; 1-hydroxy-4,7-diphenyl-5-dodecyl-5-aza-1-bora-2,8-dioxacyclooctane; 1-hydroxy-3,7-dicresyl-5- dodecyl-5-aza-1-bora-2,8-dioxacylclooctane; 1-hydroxy-4,6-dicresyl-5-dodecyl-5-aza-1-bora-2,8-dioxacyclooctane; 1-hydroxy-4,7-dicresyl-5-dodecyl-5-aza-1-bora-2,8-dioxacyclooctane; 1-hydroxy-3,7-dimethyl-3,7-diphenyl-5-dodecyl-5-aza-1-bora-2, 8-dioxacyclooctane; 1-hydroxy-4,6-dimethyl-4,6-diphenyl-5-dodecyl-5-aza-1-bora-2,8-dioxacyclooctane; 1-hydroxy-4,7-dimethyl-4,7-diphenyl-5-dodecyl-5-aza-1-bora-2,8-dioxacyclooctane; 1-hydroxy-3,7-para tertiarybutylphenyl-5-dodecyl-5-aza-1-bora-2,8-dioxacyclooctane; 1-hydroxy-4,6-para tertiarybutylphenyl-5-dodecyl-5-aza-1-bora-2,8-dioxacyclooctane; 1-hydroxy-4,7-para tertiarybutylphenyl-5-dodecyl-5-aza-1-bora-2,8-dioxacyclooctane; 1-hydroxy-3,7-diphenyl-5-coco-5-aza-1-bora-2,8-dioxacyclooctane; 1-hydroxy-4,6-diphenyl-5-coco-5-aza-1-bora-2,8-dioxacyclooctane; 1-hydroxy-4,7-diphenyl-5-coco-5-aza-1-bora-2,8-dioxacyclooctane; 1-hydroxy-4,6-diphenyl-5-tallow-5-aza-1-bora-2,8-dioxacyclooctane; 1-hydroxy-4,7-diphenyl-5-tallow-5-aza-1-bora-2,8-dioxacyclooctane; and 1-hydroxy-3,7-diphenyl-5-tallow-5-aza-1-bora-2,8-dioxacyclooctane and mixtures thereof.

4. The lubricating composition defined in claims 1 or 3 wherein x is a metal selected from the group consisting of scandium, titanium, vanadium, chromium, manganese, iron, cobalt, nickel, copper, zinc, tin and lead and mixtures thereof.

5. The lubricating composition defined in claim 1 wherein the extreme pressure, anti-wear and friction reducing additive contains from 0.5 to about 10 weight percent of boron.

6. The lubricating composition defined in claim 1 wherein the extreme pressure, anti-wear and friction reducing additive contains from 1 to about 17 weight percent of a transition metal or a Group IVA metal.

7. The lubricating composition defined in claim 1 wherein the extreme pressure, anti-wear and friction reducing additive in step (A) comprises from 0.1 to about 15 weight percent of said composition.

8. The lubricating composition defined in claim 1 where $R_1$, $R_2$, $R_3$ and $R_4$ of the extreme pressure, anti-wear and friction reducing additive in step (A) are the same or different radicals selected from hydrogen or an alkyl, aryl, alkylaryl or arylalkyl radical having from 1 to about 30 carbon atoms, wherein at least two of said $R_1$, $R_2$, $R_3$ or $R_4$ are the same or different aryl, alkylaryl or arylalkyl radicals having from about 6 to about 30 carbon atoms.

9. The lubricating composition defined in claim 1 where $R_9$ and $R_{10}$ of the copper corrosion inhibitor in step (B) are the same or different moieties selected from hydrogen or straight or branched chain alkyl, cyclic or alicyclic alkyl, aryl, alkylaryl or arylalkyl radicals having from about 4 to about 16 carbon atoms, provided that $R_9$ and $R_{10}$ are not both hydrogen.

10. The lubricating composition defined in claim 1 wherein the copper corrosion inhibitor in step (B) is a member selected from the group consisting of 1,3,4-thiadiazole-2,5-bis (octyldisulfide); 1,3,4-thiadiazole-2,5 bis(octyltrisulfide); 1,3,4-thiadiazole-2,5 bis (octyltetrasulfide); 1,3,4-thiadiazole-2,5 bis (dodecyldisulfide); 1,3,4-thiadiazole-2,5 bis (dodecyltrisulfide); 1,3,4-thiadiazole-2,5 bis (dodecyltetrasulfide); 2-lauryldithia-5-thiaalpha-methylstyryl-1,3,4 thiadiazole; 2-lauryltrithia-5-thiaalpha-methylstyryl-1,3,4 thiadiazole; 2 mercapto-5 octyldithio-1,3,4-thiadiazole and 2 mercapto-5 dodecyldithio-1,3,4-thiadiazole and mixtures thereof.

11. The lubricating composition defined in claim 1 where the copper corrosion inhibitor in (B) comprises from 0.001 to about 5 weight percent of said composition.

12. The lubricating composition defined in claim 1 where the terephthalic acid in (C) comprises from 0.001 to about 1 weight percent of said composition.

13. The lubricating composition defined in claim 1 where the oxidation inhibitor in (D) is a metal derivative of bis(dithiobenzil) selected from the group consisting of bis(dithiobenzil) iron, bis(dithiobenzil) cobalt, bis(dithiobenzil) nickel, bis(dithiobenzil) copper, bis (dithiobenzil) zinc, bis(dithiobenzil) vanadium, bis (dithiobenzil) chromium and bis(dithiobenzil) manganese and mixtures thereof.

14. The lubricating composition defined in claim 1 wherein the oxidation inhibitor in (D) comprises from 0.01 to about 1 weight percent of said composition.

15. A lubricating composition comprising a major amount of a lubricating oil and a minor amount of:
(A) The reaction products which form by reacting boric acid in about a 1:1 molar ratio with the intermediate reaction products which form by reacting a primary amine or ammonia in about a 1:2 molar ratio with an aromatic oxide of the formula:

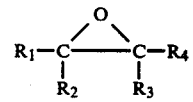

where at least one of said $R_1$, $R_2$, $R_3$ or $R_4$ is aryl, alkylaryl or arylalkyl having from about 6 to about 30 carbon atoms with the remaining R groups being independently hydrogen or an organic radical having from 1 to about 30 carbon atoms;

(B) A copper corrosion inhibitor comprising a compound having the formula:

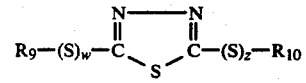

wherein $R_9$ and $R_{10}$ are moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different integers between 1 and 8;

(c) A lead corrosion inhibitor comprising terephthalic acid; and (D) An oxidation inhibitor comprising a metal additive having the formula:

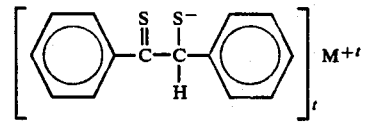

where M is a first row transistion metal and t is an integer between 1 and 4.

16. The lubricating composition defined in claim 15 where the primary amine in (A) has from 1 to about 24 carbon atoms.

17. The lubricating composition defined in claim 15 where the primary amine in (A) is a member selected from the group consisting of methylamine, ethylamine, propylamine, butylamine, octadecylamine, cyclohexylamine, phenylamine, dodecylamine, oleylamine, hexadecylamine, cocoamine, and tallowamine and mixtures thereof.

18. The lubricating composition defined in claim 15 where at least two of $R_1$, $R_2$, $R_3$ or $R_4$ in (A) are aryl, alkylaryl, or arylalkyl having from about 6 to about 30 carbon atoms with the remaining R groups being independently hydrogen or an alkyl radical having from 1 to about 6 carbon atoms.

19. The lubricating composition defined in claim 14 where the aromatic oxide in (A) is a member selected from the group consisting of styrene oxide, alpha methyl styrene oxide, para tertiary butyl styrene oxide and cresyl oxide and mixtures thereof.

20. The lubricating composition defined in claim 15 where the intermediate reaction products in (A) comprise an aryloxylated primary amine.

21. The lubricating composition defined in claim 15 where the intermediate reaction products in (A) comprise a diaryloxylated amine.

22. The lubricating composition defined in claim 15 where the reaction products in (A) comprise from 0.1 to about 15 weight percent of said composition.

23. The lubricating composition defined in claim 15 where $R_9$ and $R_{10}$ of the copper corrosion inhibitor in (B) are moieties selected from hydrogen or straight or branched chain alkyl, cyclic or alicyclic alkyl, aryl, alkylaryl or arylalkyl radicals having from about 4 to about 16 carbon atoms and w and z are the same or different integers between 1 and 4.

24. The lubricating composition defined in claim 15 where the copper corrosion inhibitor in (B) is a hydrocarbon polysulfide derivative of 2,5-dimercapto-1,3,4-thiadiazole selected from the group consisting of 1,3,4-thiadiazole-2,5-bis (octyldisulfide); 1,3,4-thiadiazole-2,5 bis(octytrisulfide); 1,3,4-thiadiazole-2,5 bis (octyltetrasulfide); 1,3,4-thiadiazole-2,5 bis (dodecyldisulfide); 1,3,4-thiadiazole-2,5 bis (dodecyltrisulfide); 1,3,4-thiadiazole-2,5 bis (dodecyltetrasulfide); 2-lauryldithia-5-thiaalpha-methylstyryl-1,3,4 thiadiazole; or 2-lauryltrithia-5-thiaalpha-methylstyryl-1,3,4 thiadiazole; 2 mercapto, 5-octyldithio-1,3,4-thiadiazole and 2 mercapto, 5-dodecyldithio-1,3,4-thiadiazole and mixtures thereof.

25. The lubricating composition defined in claim 15 where the copper corrosion inhibitor in (B) comprises from 0.001 to about 5 weight percent of said composition.

26. The lubricating composition defined in claim 15 where the lead corrosion inhibitor in (C) comprises from 0.001 to about 1 weight percent of said composition.

27. The lubricating composition defined in claim 15 where M in (D) is a metal selected from the group consisting of iron, cobalt, nickel, copper, zinc, vanadium, chromium and manganese and mixtures thereof.

28. The lubricating composition defined in claim 15 where the metal derivative of bis(dithiobenzil) in (D) is a member selected from the group consisting of bis (dithiobenzil) iron; bis (dithiobenzil) cobalt; bis (dithiobenzil) nickel; bis (dithiobenzil) copper, bis (dithiobenzil) zinc; bis (dithiobenzil) vanadium; bis (dithiobenzil) chromium; and bis (dithiobenzil) manganese and mixtures thereof.

29. The lubricating composition defined in claim 15 where the oxidation inhibitor in (D) comprises from 0.01 to 1 weight percent of said composition.

30. A lubricating composition comprising a major amount of a lubricating oil and a minor amount of:
(A) The reaction products which form by reacting boric acid, in about a 1:1 molar ratio, with the intermediate reaction products which form by reacting a primary amine or ammonia in about a 1:2 molar ratio with an aromatic oxide of the formula:

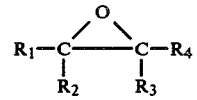

where at least two of said $R_1$, $R_2$, $R_3$ or $R_4$ are aryl, alkylaryl or arylalkyl groups having from about 6 to about 30 carbon atoms with the remaining R groups being independently hydrogen or an organic radical having from 1 to about 30 carbon atoms;
(B) a polysulfide derivative of 2,5-dimercapto-1,3,4-thiadiazole derived from the reaction of 2,5-dimercapto-1,3,4-thiadiazole with a mono or di-sulfenyl chloride;
(C) Terephthalic acid; and
(D) A bis (dithiobenzil) metal derivative derived from the reaction of
a metal halide with the intermediate product of benzoin with phosphorus sulfide in the presence of dioxane.

31. The lubricating composition defined in claim 30 where the primary amine in (A) has from 1 to about 24 carbon atoms.

32. The lubricating composition defined in claim 30 where the primary amine in (A) is a member selected from the group consisting of methylamine, ethylamine, propylamine, butylamine, octadecylamine, cyclohexylamine, phenylamine, dodecylamine, oleylamine, hexadecylamine, cocoamine, and tallowamine and mixtures thereof.

33. The lubricating composition defined in claim 30 where at least two of $R_1$, $R_2$, $R_3$ or $R_4$ in (A) are aryl, alkylaryl, or arylalkyl having from about 6 to about 30 carbon atoms with the remaining R groups being independently hydrogen or an alkyl radical having from 1 to about 6 carbon atoms.

34. The lubricating composition defined in claim 30 where the aromatic oxide in (A) is a member selected from the group consisting of styrene oxide, alpha methyl styrene oxide, para tertiary butyl styrene oxide and cresyl oxide and mixtures thereof.

35. The lubricating composition defined in claim 30 where the intermediate reaction products in (A) comprise an aryloxylated primary amine.

36. The lubricating composition defined in claim 30 where the intermediate reaction products in (A) comprise a diaryloxylated amine.

37. The lubricating composition defined in claim 30 where the reaction products in (A) comprise from 0.1 to about 15 weight percent of said composition.

38. The lubricating composition defined in claim where the polysulfide derivative in (B) is a hydrocarbon polysulfide erivative of 2,5-dimercapto-1,3,4,-thiadiazole.

39. The lubricating composition defined in claim where the polysulfide derivative in (B) comprises from 0.001 to about 5 weight percent of said composition.

40. The lubricant composition defined in claim 30 where the polysulfide derivative of 2,5-dimercapto-1,3,4-thiadiazole in (B) comprises from 0.001 to 1 weight percent of said composition.

41. The lubricating composition defined in claim 30 where the metal halide in (D) includes a metal selected from the group consisting of iron, cobalt, nickel, copper, zinc, vanadium, chromium and manganese and mixtures thereof.

42. The lubricating composition defined in claim 30 where the bis(dithiohenzil) metal derivative in (D) comprises from 0.01 to 1 weight percent of said composition.

43. A lubricating composition comprising a major amount of a lubricating oil and a minor amount of:
(A) A metal derivative of a boron-containing heterocyclic compound derived by reacting in about 1:1 molar ratio, boric acid with the intermediate reaction products which form by reacting a primary amine or ammonia in about a 1:2 molar ratio with an aromatic oxide of the formula:

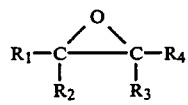

where at least one of said $R_1$, $R_2$, $R_3$ or $R_4$ is aryl, alkylaryl or arylalkyl having from about 6 to about 30 carbon atoms with the remaining R groups being independently hydrogen or an organic radical having from 1 to about 30 carbon atoms, to produce a boron-containing heterocyclic compound, and reacting the boron-containing heterocyclic compound in a molar ratio of from about 1:4 to about 6:1 with a metal selected from the group consisting of the transistion metals having an atomic number of 21 though 30 and Group IVA metals;

(B) A copper corrosion inhibitor comprising a compound having the formula:

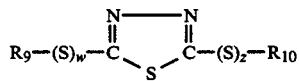

wherein $R_9$ and $R_{10}$ are moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different intergers between 1 and 8;

(C) A lead corrosion inhibitor comprising terephthalic acid; and
(D) An oxidation inhibitor comprising a metal additive having the formula:

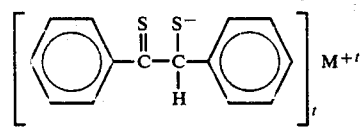

where M is a first row transition metal and t is an interger between 1 and 4.

44. The lubricating composition defined in claim 43 where x is a metal selected from the group consisting of scandium, titanium, vanadium, chromium, manganese, iron, cobalt, nickel, copper, zinc, tin, lead and mixtures thereof.

45. A lubricating composition comprising a major amount of a lubricating oil and a minor amount of:
(A) A metal derivative of a boron-containing heterocyclic compound derived by reacting boric acid in about a 1:1 molar ratio with the intermediate reaction products which forms by reacting a primary amine or ammonia in about a 1:2 molar ratio with an aromatic oxide of the formula:

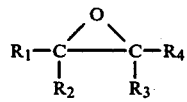

where at least two of said $R_1$, $R_2$, $R_3$ or $R_4$ are aryl, alkylaryl or arylalkyl groups having from about 6 to about 30 carbon atoms with the remaining R groups being independently hydrogen or an organic radical having from 1 to about 30 carbon atoms, to produce a boron-containing heterocyclic compound, and reacting the boron-containing heterocyclic compound in a molar ratio of from about 1:4 to about 6:1 with a metal selected from the group consisting of transistion metals having an atomic number of 21 thorugh 30 and Group IVA metal;

(B) A polysulfide derivative of 2,4-dimercapto-1,3,4-thiadiazole derived from the reaction product of 2,5-dimercapto-1,3,4,-thiadiazole with a mono or di-sulfenyl chloride;

(C) Terephthalic acid; and (D) A bis (dithiobenzil) metal derivative derived from the reaction product of a metal halide with the intermediate product of benzoin with phosphorus sulfide in the presence of dioxane.

46. The lubricating composition defined in claim 45 where x is a metal selected from the group consisting of scandium, titanium, vanadium, chromium, manganese, iron, cobalt, nickel, copper, zinc, tin, lead and mixtures thereof.

* * * * *

UNITED STATES PATENT AND TRADEMARK OFFICE
CERTIFICATE OF CORRECTION

PATENT NO. : 4,490,265
DATED : December 25, 1984
INVENTOR(S) : Richard A. Holstedt and Peter Jessup It is certified that error appears in the above-identified patent and that said Letters Patent are hereby corrected as shown below:

In column 23, line 14, change "14" to -- 15 --.

In column 24, line 65, after "claim" insert -- 30 --.

In column 24, line 67, change "erivative" to -- derivative --.

In column 25, line 1, after "claim" insert -- 30 --.

In column 25, line 4, change "lubricant" to -- lubricating --.

In column 26, line 44, change "thorugh" to -- through --.

Signed and Sealed this

Twenty-third Day of July 1985

[SEAL]

Attest:

DONALD J. QUIGG

Attesting Officer    Acting Commissioner of Patents and Trademarks